US006737238B2

(12) United States Patent
Suzuki et al.

(10) Patent No.: US 6,737,238 B2
(45) Date of Patent: May 18, 2004

(54) SUBSTRATE MEASURING METHOD AND DEVICE

(75) Inventors: Tomohiro Suzuki, Sagamihara (JP); Tadashi Okamoto, Yokohama (JP); Kazuhiro Matsumoto, Utsunomiya (JP); Nobuko Yamamoto, Isehara (JP)

(73) Assignee: Canon Kabushiki Kaisha, Tokyo (JP)

( * ) Notice: Subject to any disclaimer, the term of this patent is extended or adjusted under 35 U.S.C. 154(b) by 0 days.

(21) Appl. No.: 09/764,419

(22) Filed: Jan. 19, 2001

(65) Prior Publication Data

US 2003/0199097 A1 Oct. 23, 2003

(30) Foreign Application Priority Data

Apr. 16, 1999 (JP) ............................................ 11-110049

(51) Int. Cl.[7] .......................... C12Q 1/68; C12P 19/34; C07H 21/02; C07H 21/04; C07H 19/00
(52) U.S. Cl. .......................... 435/6; 435/7.1; 435/91.1; 435/91.2; 536/22.1; 536/23.1; 536/24.3; 536/24.31; 536/24.32; 536/24.33
(58) Field of Search ........................... 435/6, 7.1, 91.1, 435/91.2, 287.2; 422/68.1, 94, 86, 44, 172; 536/22.1, 23.1, 24.3–24.33

(56) References Cited

U.S. PATENT DOCUMENTS 5,922,617 A * 7/1999 Wang et al.
6,252,241 B1 * 6/2001 Sarussi .................... 250/559.4

FOREIGN PATENT DOCUMENTS

WO    WO 00/68668    11/2000

OTHER PUBLICATIONS

Weuler et al NAR vol. 25 No. 14 pp. 2793–2799 1997.*
U.S. patent application Ser. No. 09/764,049, Suzuki et al., filed Jan. 19, 2001.

* cited by examiner

Primary Examiner—Jeffrey Siew
(74) Attorney, Agent, or Firm—Fitzpatrick, Cella, Harper and Scinto

(57) ABSTRACT

To provide a method of making measurements for a sample on the measuring surfaces of a substrate which makes it possible to simplify the control and construction of a measuring device, shorten the measuring period, make the measuring conditions constant, and improve the positional accuracy. The method and a device for carrying out the method are characterized in that measurements for the sample is performed by forming a circular orbit of detection areas, where detection is performed with a detector, on the measuring surfaces of the substrate while moving the detection areas relative to the substrate.

18 Claims, 3 Drawing Sheets

Substrate Rotating Direction

Substrate Horizontally Moving Direction

SUBSTRATE MEASURING METHOD AND DEVICE

BACKGROUND OF THE INVENTION

1. Field of the Invention

This invention relates to a method and device for making measurements on the surface of a substrate, in particular, to a method and device for making measurements for portions to be measured on a substrate using scan operation (scanning).

2. Related Background Art

In recent years, with the development of biotechnology, there have been increasing needs for making measurements for and detection of the samples from living organisms. The samples from living organisms are, in general, often hard to carry out a close measurement, unlike chemical substances obtained using the technique of synthetic chemistry, because 1. they has extremely wide variegation;
2. their absolute quantity is small; and
3. those having similar physical properties must be distinguished.

To date there have been devised various methods of making measurements for such samples; and among them, the measurements using a solid phase substrate are receiving most attention now. The measuring technique using a solid phase substrate is, for example, such that it allows detection probes (for example, antibody) fixed on or absorbed into a substrate to react with a sample labeled with a fluorescent substance (for example, antigen) on the substrate and makes measurements for the sample by observing the fluorescence on the substrate.

The principal reasons (advantages) that this measuring technique attracts particular attention are, for example, as follows:

1. measurements can be performed for an infinitely small amount of sample by decreasing the amount (area) of the detection probes attached on the substrate, and hence, the absolute quantity of the sample is not required to be large;
2. measurements of multiple items can be performed simultaneously by arraying various detection substances on the substrate; and
3. the substrate is easy to handle because it is not in a liquid phase, but in a solid phase.

The measurements for a sample using a solid-phase substrate have been applied, for example, to the detection of the base sequences of nucleic acids. In such a detection operation, first, various types of single-stranded DNAs (DNA probes) with various base sequences are attached on a substrate in an array and then a DNA labeled with, for example, fluorescent pigment is applied thereto. When there exists in the sample a sequence complementary to the DNA probe on the substrate, the fluorescent substance is adsorbed on the substrate (hybridization); thus, the base sequence contained in the sample can be examined by checking the state of hybridization against the DNA probe on the substrate. As a matter of fact, Affymertrix in the U.S has developed a DNA chip such that as many as about 10,000 types of DNA probes are arrayed on its micro-area by the photolithographic process and has applied the same to the analysis of DNA base sequences.

An area on which each probe is attached in an array consists of extreme-micro-areas. The reason for this is that, when the absolute quantity of the sample is small, a highly sensitive detection is made possible by concentrating the sample on a micro-probe-area so as to allow the amount of sample per unit to be larger, that is, to provide higher sample density.

Scattering the sample on a wide-probe-area lower a detection sensitivity.

Accordingly, detectors for use in the observation of such arrays are often microscopes or devices including a cofocal optical system. In such cases, the whole of the array is not subjected to analyzing and measuring processing, but it needs to be divided into micro-areas and subjected to read processing area by area with a microscope with high magnification. In other words, detectors involving scan operation are needed. Scanning methods include, for example, methods to perform scan operation by moving a light detecting portion over a substrate having certain dimensions and by moving a substrate while fixing a light detecting portion. Thus various types detectors have been designed so as to match various types scanning methods.

For example, an exclusive detector is commercially available from Hewlet Packard which is a device for making measurements for the DNA microarrays by Affymetrix, and this device consists of both a cofocal optical system and a scanner.

In scanners in common use, for example when the substrate to be measured is rectangular, read operation is performed by scanning from one end of the substrate linearly in a fixed direction to the other end and then returning so as to scan the next area, and repeating this motion. In other words, the scan operation involves a reciprocating motion in terms of its scanning direction (scan operation is not performed in one direction, but involves a returning motion).

However, scan operation involving a reciprocating motion gives rise to problems of making the control and construction of the device more complicated and requiring a longer measuring period. The longer measuring period gives rise to another problem of creating a difference in measuring conditions between the areas of the first measurement and the last measurement. In order to prevent this problem, a special device needs to be installed. Further, detection is performed using fluorescent pigments, the problems of color fading and denaturation may occur depending on the pigment.

A discontinuous scan operation involving a returning motion attendant to a reciprocating motion is likely to cause a decrease in positional accuracy compared with a continuous scan operation. This may affect the measurements on the substrate consisting of high-density microarrays.

SUMMARY OF THE INVENTION

Accordingly, the object of the present invention is to solve the problems attendant to the above scanning method.

Specifically, an object of the present invention is to provide a method of making measurements for the sample on the measuring surface of the substrate, comprising forming a circular orbit of detection areas on the measuring surface of the substrate by moving the area to be detected with a detector relative to the substrate.

One example of the measuring methods described above is such that the measurements for the sample are made while forming a rotational surface of the subject and the circular orbit as described above by rotating the substrate around the axis perpendicular to the surface of the substrate on which measurements are made, in particular, the measurements are made by moving the detection area relative to the rotational surface of the substrate on which measurements are made.

Another example of the measuring methods described above is such that it performs measurements while forming the circular orbit of the measuring areas as described above by allowing the detector to perform a rotational motion.

The sample described above is fixed on, adsorbed into, or trapped in the substrate as described above and it is, for example, specifically fixed on the substrate by the probes arranged on the surface of the same.

Preferably, the probes and the sample on the substrate as described above are DNA, protein and peptide nucleic acid (PNA). The measurements for the above sample are made using luminescence such as fluorescence and chemalluminescence.

Specifically, when making measurements for the sample, any one of the absorption, transmission and reflection of the incident light to said sample is measured.

When multiple labels are detected with multiple detectors in the measurements for the above sample, the multiple labels can be detected with their corresponding detectors simultaneously.

Another object of the present invention is to provide a device for making measurements for a sample on the measuring surface of the substrate, comprising:

a detector for measuring for a label from the sample;

a means for supporting the substrate having the sample as the subject of measurements on its measuring surface; and a means for forming a circular orbit of detection areas on the measuring surface of the substrate by moving the detection areas, in which detection is performed with a detector, relative to the substrate.

DETAILED DESCRIPTION OF THE PREFERRED EMBODIMENTS

Figure 1:
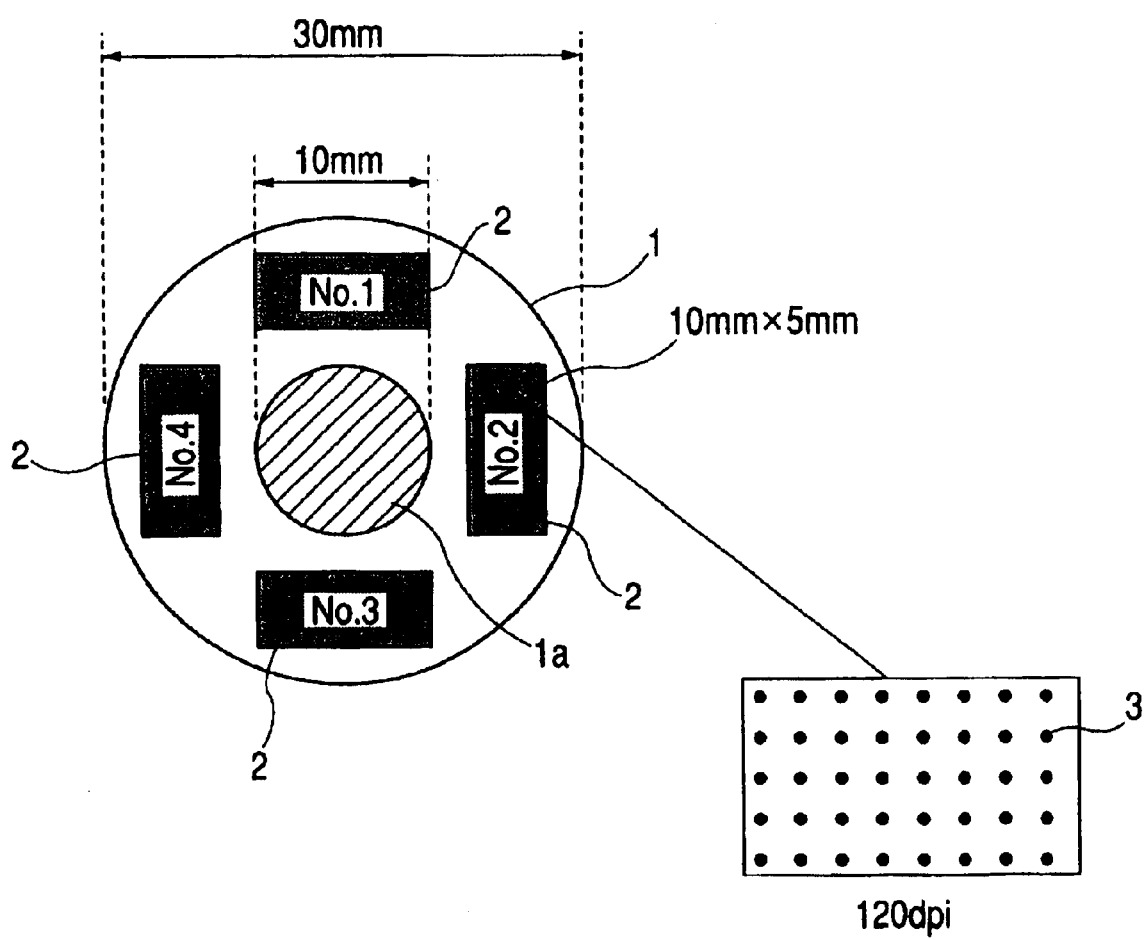
FIG. 1 is a view of a substrate on which 4 types of previously prepared DNA are printed.

The substrate measuring method and device of the present invention are characterized in that they allow a substrate, as a subject of measurements, to rotate around a certain point in a plane in which the substrate is placed and scan the measuring area of the substrate by the use of the rotational movement thereof.

The use of the rotational movement of the substrate allows the scan operation to be performed in a fixed direction while omitting the reciprocating scan operation involving stopping scanning and changing the scanning direction, which are likely to affect the accuracy of the measurement, resulting in improvement in the accuracy and speed of measurement.

As a driving system used for making measurements for the areas on the substrate, the method and device require a driving system for rotating the substrate. If measurements cannot be made for all the measuring areas by the use of the rotational movement of the substrate alone, an additional driving system for changing the radial length, from the center of the rotation to the measuring portion, is optionally installed, so as to enable the measurements for all the measuring areas.

From the standpoint of easy rotation, the substrate is desirably a special substrate which incorporates a central axis of rotation as a constituent, so that the rotational driving of the axis can be directly transmitted thereto, like data disks commonly used in daily life; however, if it is impossible to prepare such a substrate, the substrate may be rotated using a holder on which it is fixed. When the central axis of rotation cannot be incorporated in the substrate plane for the reasons related to measurement, the substrate may be rotated around the central axis established outside it while being fixed on the holder.

Generally, it is often easier to move the substrate than to move the measuring portions because of the structure of the devices; however, in cases where the substrate is difficult to rotate, a driving system may be used which does not rotate the substrate, but rotates mainly the measuring portions.

In cases where measurements need to be made for multiple items such as absorption and fluorescence, the measuring portions can be provided item by item and measurements can be performed for all the portions simultaneously.

Measurements may be made at suitable intervals while allowing the measuring portions to continuously move at a constant speed, or they may be made while stopping the substrate intermittently after allowing it to move by a predetermined distance. When rotating the substrate, desirably the rotational speed is variable so that it can be properly established depending on the necessary measuring time and resolution. When the accuracy and reliability of the data taken on a measuring portion of the substrate can be improved by integrating the measured values obtained from multiple times of measurement on the same portion, such integration may be carried out according to the situation.

The data obtained from the measurements on the measuring portions become final data in combination with, for example, the positional information obtained from the rotation angle of the substrate and the distance from the central axis of the rotation (radius). And in order to obtain more accurate positional information, desirably the measurements are performed while picking up the movements of some markers having been previously provided on or around the substrate. This enables measurements with a higher accuracy.

The method of measuring fluorescence intensity in accordance with the present invention is applicable to the detection of substances using a solid-phase substrate, to which increasing attention has been being paid in recent years. One example of the applications is the DNA chips developed by Affymetrix in the U.S., as described above. The substrate measuring method of the present invention can be used as a scanner for measuring the fluorescence or luminescence intensity on the solid-phase substrates on which various types of probes such as DNA and proteins are arrayed in high density.

EXAMPLE 1

(1) Preparation of Substrate

A silica glass substrate 3 cm in diameter and 0.5 mm in thickness was prepared. In order to allow the substrate to rotate, a structure capable of transmitting rotational drive was provided for the substrate on the circular portion with its center at the center of the substrate and with a diameter of 1 cm.

The silica glass substrate was water-washed lightly, and then subjected to ultrasonic cleaning for 20 minutes while being immersed in an exclusive substrate cleaning solution, and left stand one whole day and night. Then the substrate was taken from the cleaning solution so as to wash the cleaning solution away with water and deionized water, and immersed in 1 M NaOH aqueous solution having been heated to 60° C. for 20 minutes. The substrate was taken from the NaOH aqueous solution, so as to wash the NaOH aqueous solution away with water and ultrapure water, and subjected to ultrasonic cleaning in ultrapure water for 20 minutes.

Then the substrate was immersed in a silane coupling agent (manufactured by Shin-Etsu Chemical Co., Ltd., brand name: KBM 603) for one hour, which was previously dissolved in water to be 1% aqueous solution and subjected to hydrolysis for about one hour. The substrate was washed lightly with ultrapure water, dried by removing water droplets remaining on the surface with nitrogen gas, and baked in an oven at 120° C. for 2 hours. Amino groups were introduced to the surface of the glass substrate by combining the silane coupling agent with the same.

Then a crosslinking agent, EMCS (N-(Maleimidocaproyloxy) succinimide), manufactured by Dojindo Laboratories was dissolved in a mixed solvent (ethanol:DMSO=1:1) in the proportion of 3 mg to 10 ml. The glass having been baked previously was immersed in the obtained EMCS solution and left for 2 hours. After taking the substrate from the EMCS solution and washing lightly with the same mixed solvent as above, the droplets remaining on the surface of the substrate were subjected to substitution into ethanol, and the substrate was dried by removing the droplets with nitrogen gas. Thus obtained was a substrate (EMCS substrate) with the entire surface (the surface of both sides) of which EMCS was combined. EMCS contains a succinimide group and a maleimido group; and since the succinimide group reacts with the amino group on the surface of the substrate, the surface of the substrate had the maleimido group having been introduced thereon.

(2) DNA Attachment

Modified 18 mer DNAs (probes) with a thiol group (SH group) attached to one terminal thereof were synthesized by BEX at the request of the applicants of this invention. The SH group was attached to each 5' terminal and the DNA base sequences were as follows:

No. 1: $^{5'}$HS-ACTGGCCGTCGTTTTACA$^{3'}$ (SEQ. ID No. 1)

No. 2: $^{5'}$HS-ACTGGCCGTTGTTTTACA$^{3'}$ (SEQ. ID No. 2)

No. 3: $^{5'}$HS-ACTGGCCGCTTTTTTACA$^{3'}$ (SEQ. ID No. 3)

No. 4: $^{5'}$HS-ACTGGCATCTTGTTTACA$^{3'}$ (SEQ. ID No. 4)

The above DNAs were dissolved in SG Clear (aqueous solution containing 7.5% of glycerol, 7.5% of urea, 7.5% of thiodiglycol and 1% of Acetylenol EH (manufactured by Kawamura Fine Chemicals)), which is a solvent for use in thermal jet printer (Bubble jet printer=BJ printer), and adjusted to a final concentration of 8 $\mu$M. And a cartridge for use in ink jet printers is filled with the DNA solution. The four types of probes are arranged in the pattern shown in FIG. 1. Each type of probe consists of an area 2 of 5 mm×10 mm, and are arranged each area a probe 3 of the same type in 120 dpi density.

Then the substrate with the DNA solution placed thereon was left in a humidifying chamber for 30 minutes to react the substrate with DNA.

The BJ printer used was a remodeled type of BJ printer BJC-600, which is manufactured by Canon Inc. and capable of doing litho printing, and the amount of the DNA solution discharged per dot was 24 picoliters.

After completion of the reaction, the substrate was rinsed with 1M NaCl/50 mM phosphate buffer solution (pH 7.0), so as to wash the DNA solution on the surface of the glass away completely. Then the substrate was immersed in 2% bovine serum albumin aqueous solution, left for 2 hours, and subjected to blocking reaction. After the blocking reaction, the substrate was again rinsed with 1M NaCl/50 mM phosphate buffer solution (pH 7.0), so as to obtain the substrate to which DNAs were attached.

(3) Hybridization

A DNA labeled with Rhodamine was synthesized which had Rhodamine having been attached to 5' terminal thereof and had a complementary sequence to the probe No. 1. This synthesis was also carried out by BEX at the request of the applicants of this invention. This labeled DNA was dissolved in 1M NaCl/50 mM phosphate buffer solution (pH 7.0) so as to obtain a final concentration of 1 $\mu$M, and 2 ml of the obtained solution was sealed into a hybridization package together with the substrate, so as to subject them to hybridization reaction for 3 hours.

Then the substrate 1 was rinsed with 1M NaCl/50 mM phosphate buffer solution (pH 7.0) to obtain the substrate as the subject of measurements.

(4) Device Construction

Figure 2:
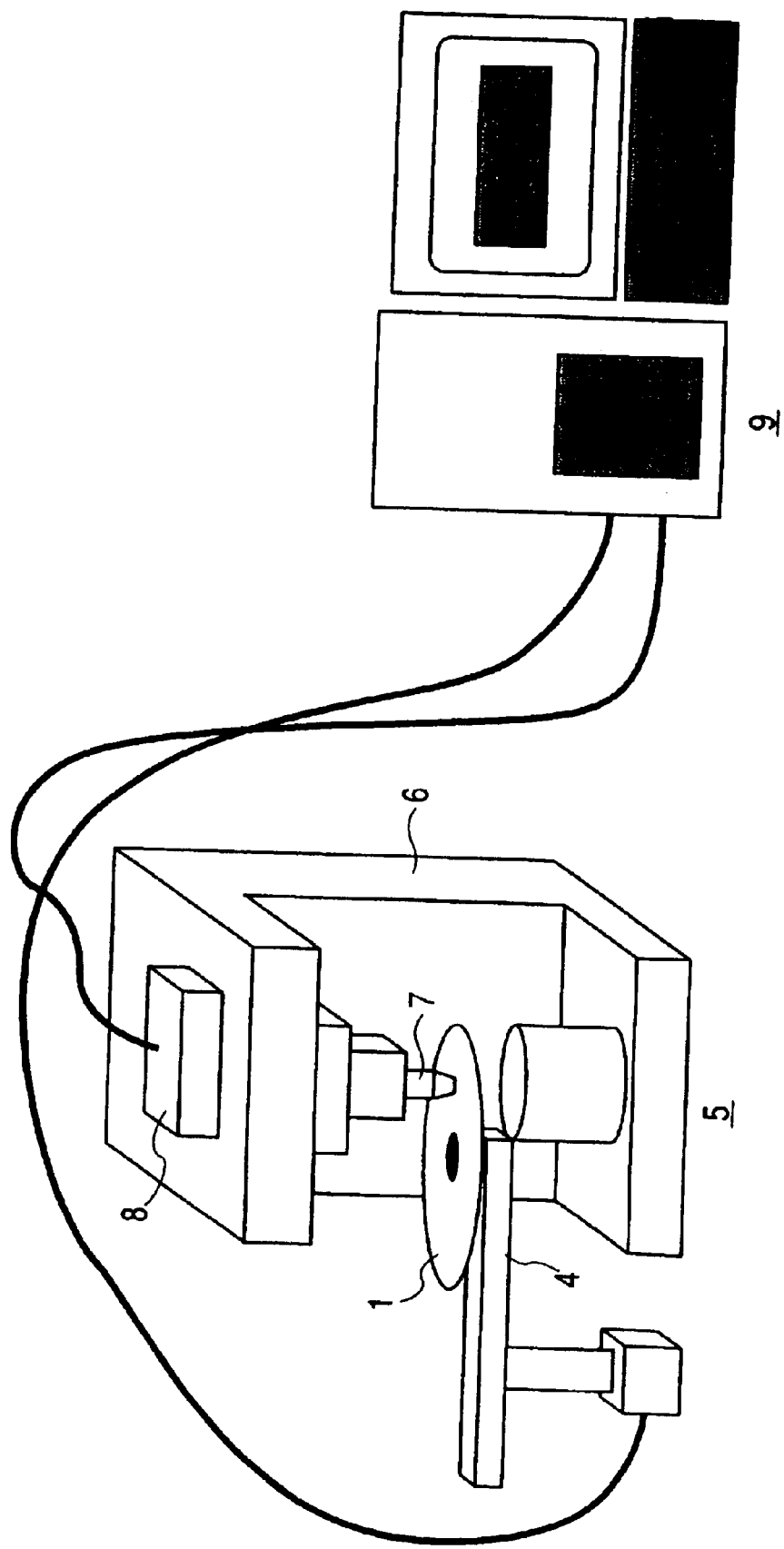
FIG. 2 is a view of a substrate measuring device.
Figure 3:
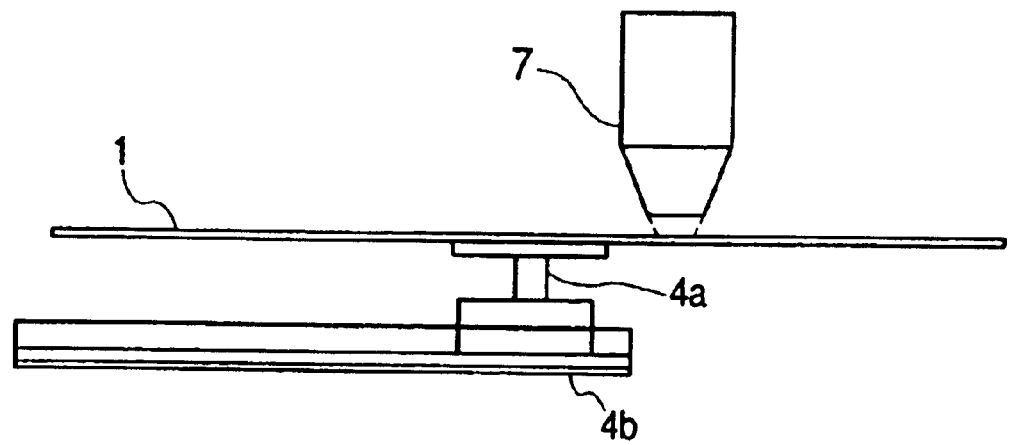
FIG. 3 is an enlarged view of the stage portion of a substrate measuring device.

The stage portion of a fluorescence microscope manufactured by Nikon Corporation was remodeled, and a stage 4 shown in FIG. 2 was fixed to the fluorescence microscope. The stage 4 consisted of a rotational drive stage 4a for rotating the substrate 1 and a horizontal drive stage 4b for allowing the same to move horizontally. FIG. 3 shows the details of the stage portion. The stage portion was remodeled so that any desired portion of the measuring areas on the substrate could be set under the object lens 7 of the fluorescence microscope 5 by properly controlling the two driving devices.

The two driving devices were designed in such a manner that they could output their respective positional information to an image processing apparatus 9 and the image processing apparatus could pick up the positions on the substrate for which measurements were being made with the lens.

For the light source 6 of the fluorescence microscope, a mercury lamp in common use was used. A filter and a dichroic mirror were configured in such a manner that the wave lengths of excitation light and fluorescence were from 455 nm to 595 nm and from 610 nm to 725 nm, respectively. The fluorescence obtained was output into the image processing apparatus via a detector 8 and subjected to proper image processing in combination with the positional information output from the stage. In other words, the entire image of the measuring areas on the substrate could be displayed by superimposing the images obtained from the detector based on the positional information sent from the stage.

(5) Substrate Measurement

Figure 4:
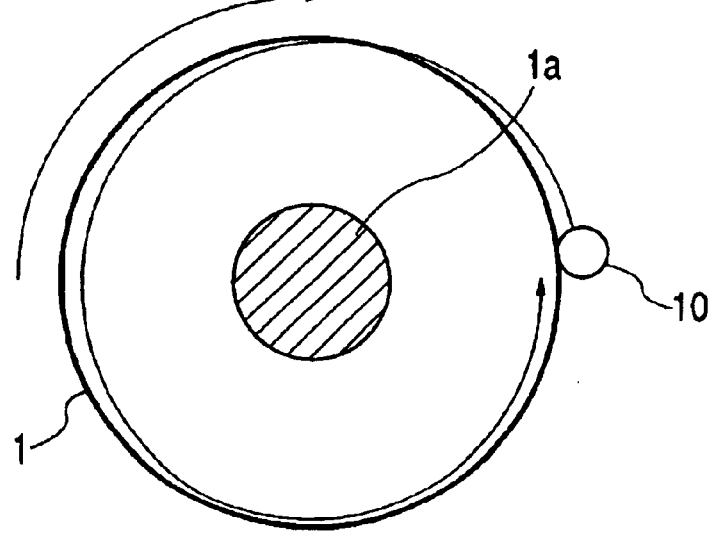
FIG. 4 is a view showing the scanning process in measuring areas.

After fixing the substrate 1 to the holder of the stage and bringing the same into focus, the two driving devices were started so as to perform measurements. The scanning method was established so that scanning could be performed from the periphery of the substrate spirally inward by decreasing the spacing between the central axis of the substrate and the object lens while allowing the substrate to rotate clockwise (refer to FIG. 4). In order to make possible the measurements for all the measuring areas on the substrate by allowing the detector to scan the measuring areas 10, the two driving devices were properly controlled, in addition, the rotational speed of the disk was set for the CLV method (constant linear velocity method) so as to uniformize the reading accuracy.

For the object lens, a lens of 40 magnifications was used, and it was set in such a manner that one spot became a circle with a diameter 5 µm. The rotational speed was set in such a manner that the liner velocity was always 500 mm/s and controlled so that the spacing between the rotational axis and the object lens was decreased by 5 µm each time the disk made one rotation.

For the detector, a photomultiplier tube equipped with a barrier filter was used. The signal detected was sent to the image processing apparatus as an electric signal of one dimension, and the data was processed in combination with the positional information from the disk.

After the measurements with the image processing apparatus, images were obtained which were nearly equivalent to those expected from the print patterns and the sequences of the probes. Specifically, in the area of No. 1 where the sequences of the probe and the sample were completely complementary to each other, intensive fluorescence was detected. In the areas of No. 2 and No. 3, less intensive fluorescence patterns were obtained, and in the area of No. 4, almost no fluorescence was detected.

The patterns obtained from the areas of No. 1, No. 2 and No. 3 were in accord with the print patterns when preparing the substrate.

The determination of the average intensity of fluorescence for each probe on the image processing apparatus showed that, in the probe No. 1 having a sequence completely matching that of the labeled DNA, the fluorescence yield was 4600, and in the probe No. 2 of which sequence had one mismatched base, the fluorescence yield was 2800. Further, in the probe No. 3 of which sequence had 3 mismatched bases, the fluorescence yield was as small as 2100, which was less than half of the fluorescence yield of the completely matched sequence. In the probe No. 4 of which sequence had 6 mismatched bases, fluorescence was hardly observed.

As described above, substrate measurements could be performed accurately and quantitatively using the method in accordance with the present invention.

The substrate measuring method in accordance with the present invention offers the advantage that substrate measurements can be performed more easily while omitting complicated scan operation. Since scan operation for making measurements for the portions on a substrate are performed by rotating the substrate, driving systems for moving the substrate can be simplified. Furthermore, the measuring method in accordance with the present invention enables the continuous scan operation in which no return motion is required, which results in high-speed and high-accuracy measurements compared with those of the methods performing discontinuous scan operation.

---

What is claimed is:

1. A method for measuring a sample on a measuring surface of a substrate, by a measuring apparatus comprising:
   rotating the substrate around an axis extending perpendicular to the measuring surface;
   moving the substrate linearly along a rotational plane of the measuring surface and measuring the sample on the measuring surface with a motionless detector.

2. The method of making measurements according to claim 1, wherein the sample is attached on, adsorbed into, or trapped in the substrate.

3. The method of making measurements according to claim 2, wherein the sample is DNA.

4. The method of making measurements according to claim 2, wherein the sample is protein.

5. The method of making measurements according to claim 2, wherein the sample is peptide nucleic acid.

6. The method of making measurements according to claim 1, wherein the sample is attached on the surface of the substrate by a probe for trapping specifically said sample.

7. The method of making measurements according to claim 6, wherein the probe is DNA.

8. The method of making measurements according to claim 6, wherein the probe is protein.

9. The method of making measurements according to claim 6, wherein the probe is peptide nucleic acid.

10. The method of making measurements according to claim 1, wherein the measurements for the sample are performed using luminescence from a label.

11. The method of making measurements according to claim 10, wherein the luminescence is fluorescence.

12. The method of making measurements according to claim 10, wherein the luminescence is chemiluminescence.

13. The method of making measurements according to claim 1, wherein measurements for the sample are performed by measuring any of the absorption, transmission and reflection of the incident light to said sample.

14. The method of making measurements according to claim 1, wherein multiple motionless detectors are used.

15. The method of making measurements according to claim 14, wherein there exist multiple labels to be detected when making measurements for the sample, the labels being detected simultaneously with the corresponding detectors.

16. A device for measuring a sample on a measuring surface of a substrate, comprising:
   a detector for measuring for a label from the sample, wherein the detector is stationary while measuring;
   a supporter to support and rotate a substrate around an axis extending perpendicular to the measuring surface; and
   a drive to move the substrate linearly along the measuring surface.

17. The device for making measurements according to claim 16, wherein the number of the detectors provided is more than one.

18. The device for making measurements according to claim 17, wherein the multiple detectors can operate simultaneously.

* * * * *

UNITED STATES PATENT AND TRADEMARK OFFICE
CERTIFICATE OF CORRECTION

PATENT NO. : 6,737,238 B2
APPLICATION NO. : 09/764419
DATED : May 18, 2004
INVENTOR(S) : Suzuki et al.

It is certified that error appears in the above-identified patent and that said Letters Patent is hereby corrected as shown below:

TITLE PAGE:
ITEM "(30)  Foreign Application Priority Data
    Apr. 16, 1999    (JP)................................... 11-110049" should be deleted.

COLUMN 1:
Line 60, "U.S" should read --U.S.--.

COLUMN 2:
Line 5, "lower" should read --lowers--.
Line 18, "detectors" should read --of detectors--.
Line 19, "scanning" should read --of scanning--.
Line 21, "Hewlet Packard" should read --Hewlett Packard--.

COLUMN 4:
Line 66, "stand" should read --to stand--.

COLUMN 7:
Line 4, "liner" should read --linear--.

COLUMN 9:
Line 15 (Claim 1, Line 4) "surface;" should read --surface; and--.
Line 19 (Claim 2, Line 1) "of making measurements" should read --for measuring--.
Line 22 (Claim 3, Line 1) "of making measurements" should read --for measuring--.
Line 24 (Claim 4, Line 1) "of making measurements" should read --for measuring--.
Line 26 (Claim 5, Line 1) "of making measurements" should read --for measuring--.
Line 28 (Claim 6, Line 1) "of making measurements" should read --for measuring--.
Line 31 (Claim 7, Line 1) "of making measurements" should read --for measuring--.
Line 33 (Claim 8, Line 1) "of making measurements" should read --for measuring--.
Line 35 (Claim 9, Line 1) "of making measurements" should read --for measuring--.
Line 37 (Claim 10, Line 1) "of making measurements" should read --for measuring--.
Line 40 (Claim 11, Line 1) "of making measurements" should read --for measuring--.

UNITED STATES PATENT AND TRADEMARK OFFICE
CERTIFICATE OF CORRECTION

PATENT NO. : 6,737,238 B2
APPLICATION NO. : 09/764419
DATED : May 18, 2004
INVENTOR(S) : Suzuki et al.

It is certified that error appears in the above-identified patent and that said Letters Patent is hereby corrected as shown below:

COLUMN 10:
Line 11 (Claim 12, Line 1), "of making measurements" should read --for measuring--.
Line 13 (Claim 13, Line 1), "of making measurements" should read --for measuring--.
Line 17 (Claim 14, Line 1), "of making measurements" should read --for measuring--.
Line 19 (Claim 15, Line 1), "of making measurements" should read --for measuring--.
Line 34 (Claim 17, Line 1), "making measurements" should read --measuring--.
Line 37 (Claim 18, Line 1), "making measurements" should read --measuring--.

Signed and Sealed this

Sixteenth Day of October, 2007

JON W. DUDAS
*Director of the United States Patent and Trademark Office*

SEQUENCE LISTING

<160> NUMBER OF SEQ ID NOS: 4

<210> SEQ ID NO 1
<211> LENGTH: 18
<212> TYPE: DNA
<213> ORGANISM: Artificial Sequence
<220> FEATURE:
<223> OTHER INFORMATION: Thiol modified DNA probe

<400> SEQUENCE: 1
actggccgtc gttttaca                                                  18

<210> SEQ ID NO 2
<211> LENGTH: 18
<212> TYPE: DNA
<213> ORGANISM: Artificial Sequence
<220> FEATURE:
<223> OTHER INFORMATION: Thiol modified DNA probe

<400> SEQUENCE: 2
actggccgtt gttttaca                                                  18

<210> SEQ ID NO 3
<211> LENGTH: 18
<212> TYPE: DNA
<213> ORGANISM: Artificial Sequence
<220> FEATURE:
<223> OTHER INFORMATION: Thiol modified DNA probe

<400> SEQUENCE: 3
actggccgct ttttaca                                                   18

<210> SEQ ID NO 4
<211> LENGTH: 18
<212> TYPE: DNA
<213> ORGANISM: Artificial Sequence

```
-continued

<220> FEATURE:
<223> OTHER INFORMATION: Thiol modified DNA probe

<400> SEQUENCE: 4
actggcatct tgtttaca                                              18
```